United States Patent [19]

Edwards

[11] Patent Number: 4,994,086
[45] Date of Patent: Feb. 19, 1991

[54] UNIVERSAL MODULAR FRAME FOR ABOVE-KNEE ENDOSKELETAL PROSTHESIS

[75] Inventor: Dan J. Edwards, Sunland, Calif. 91040

[73] Assignee: United States Manufacturing Company, Pasadena, Calif.

[21] Appl. No.: 534,334

[22] Filed: Jun. 4, 1990

Related U.S. Application Data

[63] Continuation of Ser. No. 391,428, Aug. 9, 1989, abandoned.

[51] Int. Cl.$^5$ .......................... A61F 2/72; A61F 2/62; A61F 2/66
[52] U.S. Cl. ....................................... 623/26; 623/33; 623/39; 623/52
[58] Field of Search ................. 623/26, 27, 33, 38, 623/39, 47, 50, 52

[56] References Cited

U.S. PATENT DOCUMENTS

| | | | |
|---|---|---|---|
| 3,551,915 | 1/1971 | Woodall | 623/26 X |
| 3,670,341 | 6/1972 | Webb et al. | 623/39 X |
| 4,822,363 | 4/1989 | Phillips | 623/27 |

Primary Examiner—Ronald Frinks
Attorney, Agent, or Firm—Christie, Parker & Hale

[57] ABSTRACT

A universal modular frame for use as a component in an above-knee endoskeletal prosthesis comprises a one-piece rigid outer frame of closed configuration having an upper sleeve extending between lateral and medial sides of the frame and adapted for connection to a linkage and socket for an above knee amputation, rigid lateral and medial side arms rigidly affixed to and extending downwardly from the sleeve, the lateral and medial side arms having recessed lightening recesses therein for reducing the weight of the frame, and a lower base extending between and rigidly affixed to bottom portions of the lateral and medial side arms. The outer frame forms the perimeter of an open central region for mounting a knee motion and gait control unit. The lower base has a flat bottom face and a pattern of spaced apart holes extending through the lower base for use in receiving corresponding fastening means for rigidly but releasably affixing an upper connecting portion of a lower leg pylon to the bottom of the outer frame. The lower means of attachment on the base of the frame provides a means for mounting to the frame a variety of lower leg pylons depending upon the patient's needs.

17 Claims, 2 Drawing Sheets

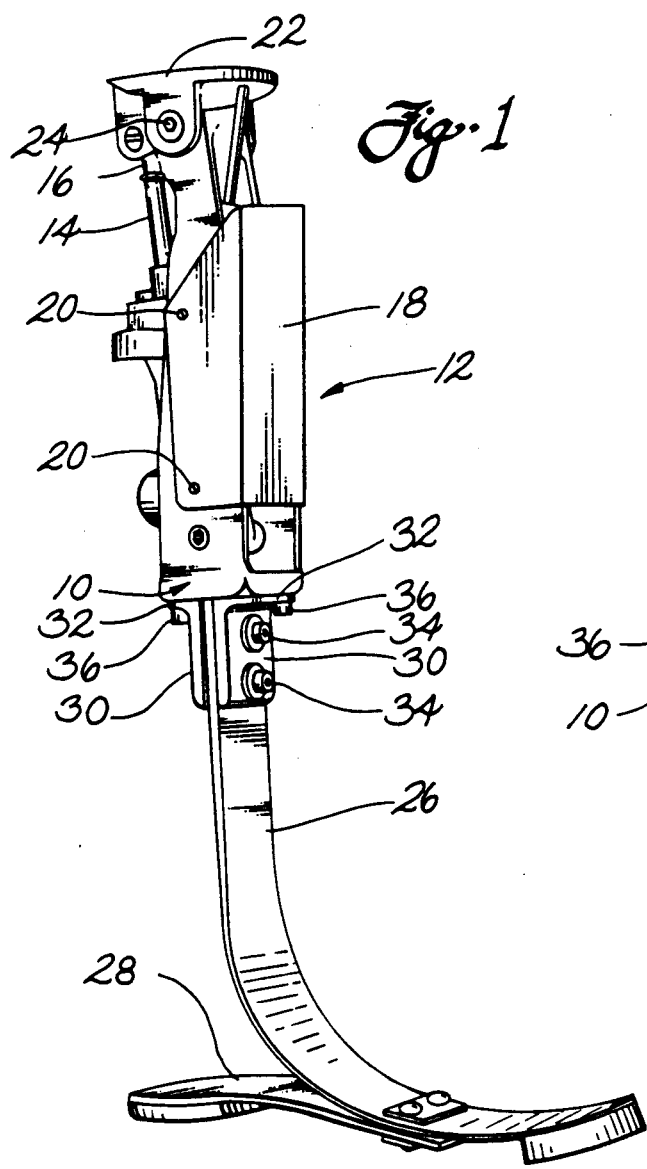
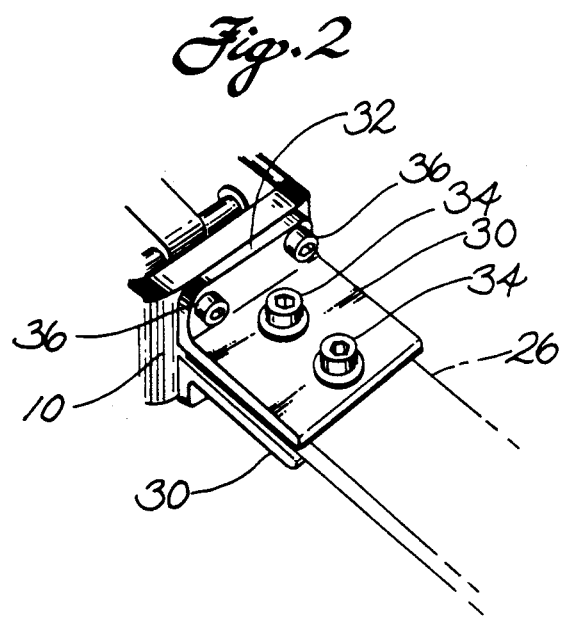
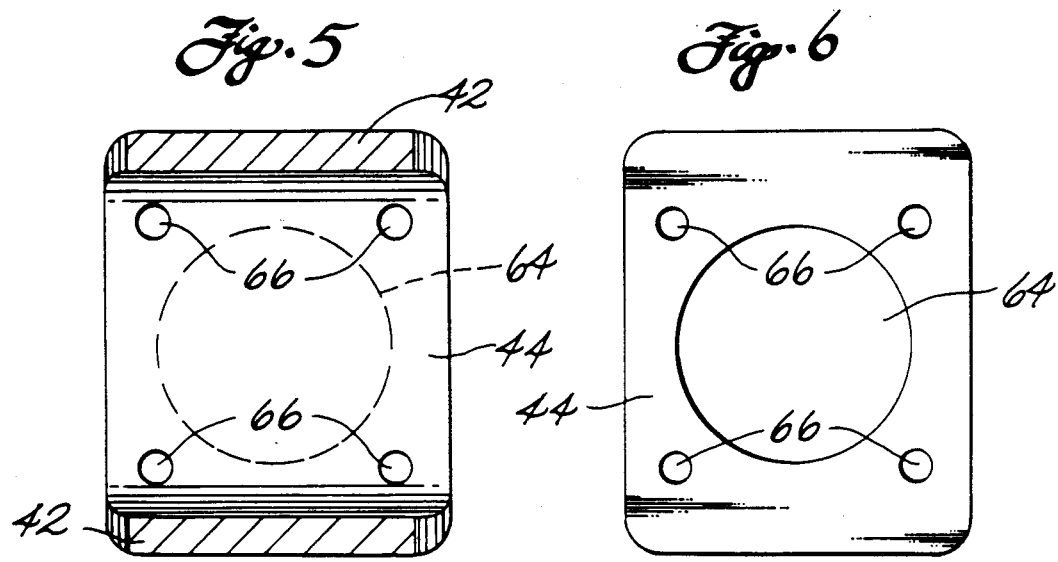

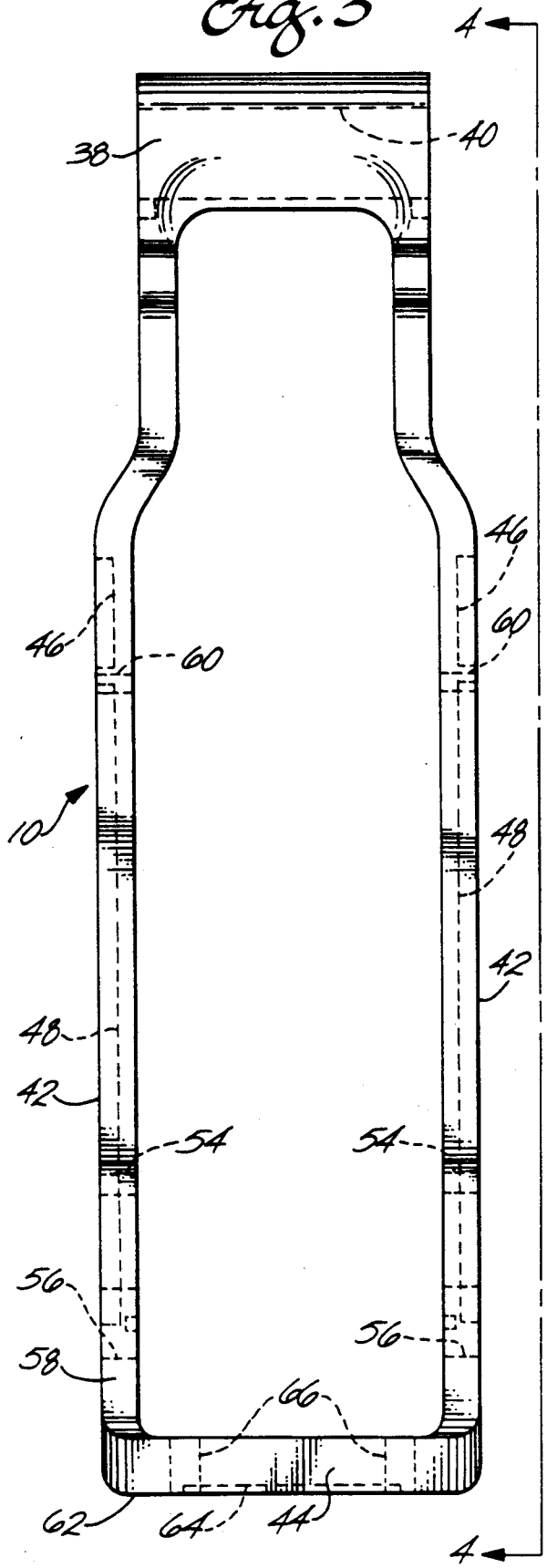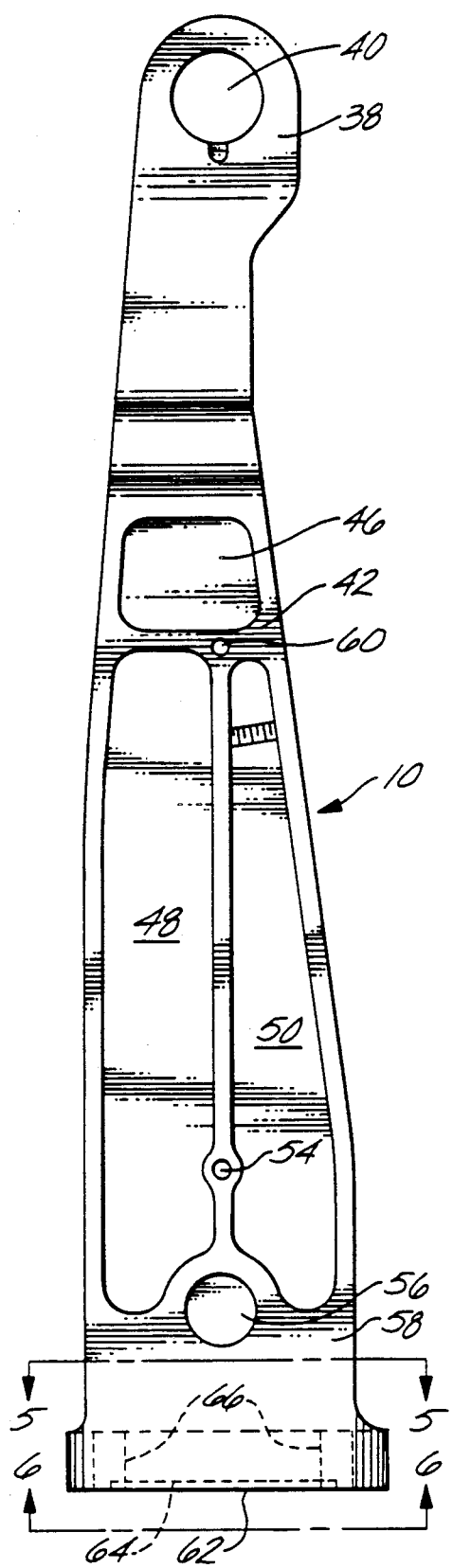

UNIVERSAL MODULAR FRAME FOR ABOVE-KNEE ENDOSKELETAL PROSTHESIS

CROSS-REFERENCE TO RELATED APPLICATIONS

This is a continuation of application Ser. No. 07/391,428, filed Aug. 9, 1989, now abandoned.

FIELD OF THE INVENTION

This invention relates to prosthetics, and more particularly to a universal modular frame for use as a component in an above knee endoskeletal prosthesis.

BACKGROUND OF THE INVENTION

In recent years, a large variety of modular prosthetic legs have been available to patients with an above knee amputation. These modular prosthetic legs have included a variety of lower leg pylons, prosthetic ankles and feet, and knee motion and gait control devices each adapted to the particular patient's needs. For instance, a lower leg prosthesis for an elderly patient will be different in its dynamic response from a lower leg prosthesis for a younger, more active patient. The various modular components used in the finished prosthesis can control such functions as heel strike, toe-off acceleration, mid-stance, swing-through, heel rise, and deceleration.

The weight of the finished prosthetic leg is a critical factor in selecting various components to be used in the prosthesis. For instance, some knee motion and gait control devices can be heavier than others, and some lower leg pylon or ankle motion devices also can weigh more than the others. As a result, some modular components that might be desirable to use in the finished prosthesis may not be used because they add too much weight to the final unit. A hydraulic gait control unit and an ankle that twists are accessories that add weight to the finished unit. These and other desirable functions of the finished prosthesis may not be possible to use if the weight added by them makes the weight of the finished prosthesis intolerable to the patient.

In addition to weight, another factor that limits use of various prosthetic components is the design of certain structural components of the brace on which the functional components are mounted. If these structural members only accept a limited number of available functional components, then the versatility of the prosthesis suffers.

The present invention provides a modular frame for an above knee endoskeletal prosthesis which is more universal in accepting a wider variety of knee control units and/or lower leg pylons while also providing a sufficient weight reduction that allows use of certain other components providing important added functions to the finished prosthesis.

SUMMARY OF THE INVENTION

Briefly, one embodiment of this invention comprises a universal modular frame for use as a component in an above knee endoskeletal prosthesis of the type which includes (a) a socket or the like for attachment to an amputated upper leg, (b) a knee motion and gait control unit, (c) a lower leg pylon or the like, and (d) a linkage between the modular frame and the socket. The modular frame comprises a rigid one-piece outer frame of closed configuration having (1) an upper connecting means extending between lateral and medial sides of the frame; (2) a rigid lateral and medial side arm each rigidly affixed to and extending downwardly from the connecting means, in which the lateral and medial side arms are recessed with lightening means for reducing the weight of the frame; and (3) a lower base extending between and rigidly affixed to the bottom portions of the lateral and medial side arms. The outer frame forms the perimeter of an open central region within the frame for mounting a knee motion and gait control unit. The lower base has a flat bottom and a pattern of spaced apart holes extending through the lower base for use in receiving corresponding fastening means for rigidly affixing an upper connecting portion of a lower leg pylon to the bottom of the outer frame. The lower base of the frame is thereby adapted to rigidly but releasably mount corresponding flanged connector means to the bottom of the frame for joining to the bottom of the frame any of a variety of lower leg pylons. The means of attachment also can facilitate mounting within the frame a variety of gait control units. The lighter frame makes it possible to produce a variety of modular lower leg prostheses from various gait control units and pylons, some of which would normally add additional weight to the unit; but the lighter weight of the frame and its universal adaptability to a variety of useful lower leg components makes the prosthesis more versatile in its function without adding an inordinate amount of weight to the overall unit.

These and other aspects of the invention will be more fully understood by referring to the following detailed description and the accompanying drawings.

BRIEF DESCRIPTION OF THE DRAWINGS

FIG. 1 is a perspective view illustrating an example of a lower leg prosthesis made from selected prosthetic components adapted for use with a universal modular frame according to principles of this invention.

FIG. 2 is a perspective view showing a lower means of attachment between the bottom of the frame and a pylon.

FIG. 3 is a front elevation view of the universal modular frame.

FIG. 4 is a side elevation view taken on line 4—4 of FIG. 3.

FIG. 5 is a cross sectional view taken on line 5—5 of FIG. 4.

FIG. 6 is an elevation view taken on line 6—6 of FIG. 4.

DETAILED DESCRIPTION

FIG. 1 is a perspective view illustrating a universal modular frame 10 used in a lower leg prosthesis 12 for an above knee amputation. This figure illustrates one of many combinations of prosthetic components that can be used with the modular frame 10. In the illustrated embodiment, a knee motion and gait control unit 14 is rigidly mounted in an interior region within the frame 10. Various gait control units can be used and this is one example. This view illustrates hydraulic shaft 16 of the gait control unit. These gait control unit shafts can be made from titanium which reduces the weight of the prosthesis while maintaining the structural strength of the unit. A shin faring 18 is mounted in a protective fashion to the front of the gait control unit by fasteners 20 attached to opposite sides of the frame. An upper knee bracket 22 is rotatably affixed to the top of the frame by a knee shaft 24 which extends through an upper connector on the frame. The knee axis shaft is aligned on and forms the knee axis of rotation for the prosthesis. The shafts of the gait control unit fasten to the bottom of the knee bracket 22 in the well known manner.

As will be better understood from the description to follow, the universal modular frame 10 of this invention provides a means for using a variety of available gait control units with the modular prosthesis 12. These choices of gait control units include the DynaPlex Hydraulic Gait Control Unit, the Locking DynaPlex Hydraulic Gait Control Unit, and the Mechanical Extension-bias Resistance Control Unit, all manufactured by United States Manufacturing Company, the assignee of this application. Knee motion and gait control units of other manufacturers also can be used with the universal modular frame 10. Other knee control units other than those described above which can be used with the modular universal frame 10 include the UCBL pneumatic, Dupaco hydraulic, SNS hydraulic, and Mortenson. Due to its unique configuration, the prosthesis can accommodate these gait control units as well as others without alterations or modifications of either the prosthesis or the knee control unit.

The modular frame also is shown attached to a lower leg pylon in the form of an energy-storing flexible foot, of the type sold by United States Manufacturing Company under the trademark FLEX-FOOT. This lower leg and foot combination comprises an elongated, flat, flexible lower leg pylon 26 and an elongated, flexible, foot 28 affixed to the bottom of the flexible pylon. The upper portion of the pylon is attached to the bottom of the frame 10 by a pair of L-shaped brackets each having an elongated flat upright leg 30 and a flat flanged upper connector 32 extending at a right angle to the lower leg 30. The brackets are placed on opposite sides of the pylon in the manner shown, and the upright leg portions of the brackets are affixed to the upper portion of the pylon by fasteners 34. The flat flanged upper connecting portions of the bracket lie flat against a flat base of the frame and are affixed to the bottom of the frame by fasteners 36. The flexible lower leg and foot combination is an example of one type of lower leg prosthesis that can be affixed to the bottom of the frame. Other examples include a lower leg prosthesis with a prosthetic ankle that twists, and a standard prosthetic lower leg pylon which can be of cylindrical configuration and can be joined to the bottom of the frame by a bracket (not shown) attached to the upper portion of the cylindrical pylon. This bracket has a flat upper flange that lies flat against the bottom of the frame 10 and is attached to the base of the frame by fasteners in a manner similar to the fasteners 36.

Detailed construction of the universal modular frame 10 is best understood by referring to FIGS. 3 through 6. The frame is preferably made from a lightweight metal such as aluminum, and the frame comprises a rigid one piece box frame of closed configuration which is generally elongated and forms a large hollow interior region bounded on all four sides by the outer frame. The frame includes a generally cylindrical upper connector portion 38. An elongated uniform diameter passage 40 which is open at both ends extends through the upper connector portion 38. A pair of elongated side arms 42 are integrally formed with opposite ends of the upper connector 38. The side arms extend downwardly along opposite sides of the frame. The side arms are identical in size and configuration. The bottoms of the side arms are integrally formed with a flat base 44. Each side arm includes a pattern of lightening recesses which, in this embodiment, include an upper recess 46 and a pair of elongated recesses 48 and 50 extending for most of the length of the side arms. A pair of mounting holes 54 for use in attaching lower portions of the shin faring 18 to the frame are aligned on a common axis and extend through lower portions of the side arms. The lightening recesses extend downwardly to and around these mounting holes. The lightening recesses are important in their weight reduction to the universal frame. The side arms also include a pair of axially aligned lower mounting holes 56 also used for attachment to the gait control unit. The outer ends of these mounting holes open through side arm portions 58 which are not recessed so that the side walls of the shin faring 18 can lie flat against these portions of the side arms and be attached to the side arms with the fasteners 20. The side arms 42 also include a pair of aligned upper holes 60 for receiving the fasteners of the shin faring.

The base 44 of the frame 10 has a flat bottom surface 62. A circular recessed area 64 faces downwardly toward the flat bottom surface 62. The recessed area 64 provides a means for seating the top of a standard size pylon bracket. A pattern of spaced apart mounting holes 66 extend through the four corners of the base. These mounting holes are preferably uniformly spaced apart on a rectangular or square pattern, and the mounting holes are each internally threaded to receive corresponding fasteners for attaching a pylon bracket to the bottom of the frame. The holes are preferably arranged on a European (metric) four-hole square pattern.

The four hole pattern provides a means for receiving mounting brackets for a wide variety of available lower leg pylons. The mounting brackets simply need to have flat, flanged upper portions which match the four hole pattern, together with some means of rigid but releasable connection to the upper portion of the pylon. This provides a substantial advantage over a previous lower leg prosthesis modular frame manufactured and sold by United States Manufacturing Company, the assignee of this application. This previous modular frame has an integral tubular extension extending downwardly from the base of the frame. This tubular extension matches only a small number of available lower leg pylons. The flat universal base of this invention also provides weight reduction, in addition to greatly improved flexibility in mounting a large number of available pylons.

With the present invention, the prosthetist is able to select from a large variety of available modular components that will fit the particular patient's needs when assembled into the finished prosthesis. The frame will house any of a wide variety of knee motion and gait control units, and the lower leg pylons also can be in a variety of configurations and functions. Many of these modular components, which control the functioning of the prosthesis, can add significant weight to the overall finished prosthesis. The modular frame, because of its lighter weight, makes it possible to use these additional components without adding significant weight that would otherwise prevent their use.

In one embodiment, the universal modular frame reduces overall weight sufficiently to permit use of a hydraulic knee motion and gait control unit and an ankle that twists on the finished lower leg prosthesis while remaining well within the tolerable weight range of about six to about eight pounds.

What is claimed is:

1. A universal modular frame for use as a shin component in an above-knee endoskeletal prosthesis of the type which includes (a) socket means for attachment to an amputated upper leg, (b) a knee motion and gait control unit, (c) lower leg pylon means, and (d) a linkage between the modular frame and the socket means;

the modular frame comprising a rigid one-piece metal outer frame of closed configuration forming a rigid skin member and having (1) an upper connecting means extending between lateral and medial sides of the frame, the upper connecting means being adapted for connecting to said linkage for the socket means, (2) rigid lateral and medial side arms rigidly affixed to and extending downwardly from the upper connecting means, said lateral and medial side arms having recessed lightning regions therein for reducing the weight of the outer frame, and (3) a lower base extending between and rigidly affixed to the bottom portions of the lateral and medial side arms;

the outer frame forming the perimeter of an open central region for rigidly but removalby mounting the knee motion and gait control unit therein;

the lateral and medial side arms being spaced apart between the upper connecting means and the lower base to form elongated open regions therebetween at both the front and rear sides of the outer frame sufficient for the knee motion and gait control unit for being inserted as a unit into said open central region of the frame from either the front or rear side of the frame;

the lower base having a flat bottom and a pattern of spaced-apart holes extending through the lower base and exposed to an underside of the lower base opposite from the control unit for use in receiving corresponding fastening means for rigidly but removably affixing a flat upper connecting portion of the lower leg pylon means to the bottom of the outer frame.

2. Apparatus according to claim 1 in which the recessed regions extend partially through the depth of the lateral and medial side walls.

3. Apparatus according to claim 1 including vertically spaced apart internally threaded shin faring holes in the lateral side arm and medial side arm of the frame, and in which there are elongated recessed lightning regions in the lateral and medial side arms on a front side and on a rear side of the vertically spaced apart shin faring holes.

4. Apparatus according to claim 3 in which the openings to the shin faring holes are on flat outer faces of the lateral and medial side arms spaced outwardly from the recessed lightning regions therein.

5. Apparatus according to claim 1 in which the holes extending through he lower base extending through four corners of the lower base on a square pattern symmetrical about a central axis through the lower base.

6. A universal modular above-knee endoskeletal prosthesis comprising:
   (a) socket means for attachment to an amputated upper leg,
   (b) a knee motion and gait control unit,
   (c) a modular frame comprising a shin component of the prosthesis,
   (d) lower leg pylon means, and
   (e) a linkage between the modular frame and the socket means,
   the modular frame comprising a rigid one-piece metal outer frame of closed configuration forming a rigid shin member and having (1) an upper connecting means extending means extending between lateral and medial sides of the frame, the upper connecting means being adapted for connection to said linkage for the socket means, (2) rigid lateral and medial side arms rigidly affixed to and extending downwardly from the upper connecting means, said lateral and medial side arms having recessed lightning regions therein for reducing the weight of the frame, and (3) a lower base extending between the rigidly affixed to the bottom portions of the lateral and medial side arms, the outer frame forming the perimeter of an open central region in which the knee motion and gait control unit is mounted;

the lateral and medial side arms being spaced apart between the upper connecting mans and the lower base to form elongated open regions therebetween at both the front side and the rear side of the outer frame sufficient for the knee motion and gait control unit to be inserted as a unit into said open central region from either the front side or rear side of the outer frame;

the lower base having a flat bottom with a pattern of spaced-apart holes extending through the lower base and exposed to an underside of the lower base opposite from the control unit for use in receiving corresponding fastening means for rigidly but removably affixing a flat upper connecting portion of the lower leg pylon means to the bottom of the outer frame.

7. Apparatus according to claim 6 in which the upper connecting portion of the lower leg pylon has a flat upper surface conforming to the flat bottom surface configuration of the frame.

8. Apparatus according to claim 6 in which the prosthesis includes a hydraulic knee motion and a gait control unit and an ankle that twists.

9. Apparatus according to claim 6 in which the lower leg pylon is secured to the lower base of the frame by a flanged bracket affixed to the pylon and to the flat bottom of the base.

10. Apparatus according to claim 6 in which the recessed regions extend partially through the depth of the lateral and medial side walls.

11. Apparatus according to claim 6 including vertically spaced apart internally threaded shin faring holes in the lateral side arm and the medial side arm of the frame, and in which there are elongated recessed lightning regions in the lateral and medial side arms on a front side and on a rear side of the vertically spaced apart shin faring holes.

12. Apparatus according to claim 11 including a shin faring secured to the shin faring holes.

13. Apparatus according to claim 11 in which the openings to the shin faring holes are on flat outer faces of the lateral and medial side arms spaced outwardly from the recessed lightning regions therein.

14. Apparatus according to claim 13 including a shin faring secured to the shin faring holes.

15. Apparatus according to claim 14 in which the recessed lightning regions comprise front and rear elongated lightning regions extending along the lateral side arm and separately along the medial side arm, each for a distance substantially the length of the shin faring.

16. Apparatus according to claim 15 in which the recessed lightning regions extend partially through the depth of the lateral and medial side walls.

17. Apparatus according to claim 6 in which the holes extending through the lower base extending through four corners of the lower base on a square pattern symmetrical about a central axis through the lower base.

* * * * *

UNITED STATES PATENT AND TRADEMARK OFFICE
CERTIFICATE OF CORRECTION

PATENT NO. : 4,994,086
DATED : February 19, 1991
INVENTOR(S) : Dan J. Edwards

It is certified that error appears in the above-identified patent and that said Letters Patent is hereby corrected as shown below:

```
Column 3, line 67, change "bottoms" to -- bottom --.

Column 5, line 9, before "member" change "skin" -- shin --.
Column 5, line 15, change "lightning" to -- lightening --.
Column 5, line 21, change "removalby" to -- removably --.
Column 5, line 44, change "lightning" to -- lightening --.
Column 5, line 51, change "lightning" to -- lightening --.
Column 5, line 53, after "through" change "he" to -- the --.
Column 5, line 68, delete "means extending" (second
          occurrence).
Column 6, lines 6,7, change "lightning" to -- lightening --.
Column 6, line 8, after "between" change "the" to -- and --.
Column 6, line 14, change "mans" to -- means --.
Column 6, lines 45,46, change "lightning" to
          -- lightening --.
Column 6, lines 53,57,58,62, change "lightning" to
          -- lightening -- (all occurrences).
```

Signed and Sealed this

Sixth Day of October, 1992

*Attest:*

DOUGLAS B. COMER

*Attesting Officer*     Acting Commissioner of Patents and Trademarks

UNITED STATES PATENT AND TRADEMARK OFFICE
CERTIFICATE OF CORRECTION

PATENT NO.  : 4,994,086

DATED       : February 19, 1991

INVENTOR(S) : Dan J. Edwards

It is certified that error appears in the above-identified patent and that said Letters Patent is hereby corrected as shown below:

Column 3, lines 26-27, delete "by United States Manufacturing Company".

Signed and Sealed this

Sixteenth Day of March, 1993

Attest:

STEPHEN G. KUNIN

*Attesting Officer*   *Acting Commissioner of Patents and Trademarks*